United States Patent [19]

Carrigan

[11] Patent Number: 5,332,871
[45] Date of Patent: Jul. 26, 1994

[54] SLIDING VALVE EAR PLUG

[76] Inventor: Noel L. Carrigan, 1713 W. Hwy. 50, Lot 88, O'Fallon, Ill. 62269

[21] Appl. No.: 811,626
[22] Filed: Dec. 23, 1991
[51] Int. Cl.[5] .............................................. A61B 7/02
[52] U.S. Cl. ..................................................... 181/135
[58] Field of Search ............... 181/129, 130, 131, 132, 181/134, 135, 137; 381/68.6, 69

[56] References Cited

U.S. PATENT DOCUMENTS

| 2,390,794 | 12/1945 | Knight | 181/135 |
| 2,754,365 | 7/1956 | Walters | 181/135 |
| 3,702,123 | 11/1972 | Macken et al. | 181/129 |
| 3,934,100 | 1/1976 | Harada | 181/135 |

Primary Examiner—Michael L. Gellner
Assistant Examiner—Khanh Dang

[57] ABSTRACT

A one of a pair earplug that has a hole through the center of it. When it is placed into a person's ear canal it enables them to hear sound from an outside source. It would be made from a material comparable to plastic. A valve in a small housing attached to the earplug is placed into their ear and ear canal to fit comfortably. The earplug, valve, and valve housing in the ear would work together to protect the wearer from loud noises only when needed and when the valve is activated to close by the wearer moving the valve fingerlatch. In the reverse when a person wanted to hear better they would manually regulate the earplug, opening the mechanical valve with the valve latch. The earplug openings would let the user hear through the hole in the earplug and valve body housing without removing the earplug. The person would then avoid losing the earplug, getting it soiled, etc. by taking it out of the ear to hear.

2 Claims, 3 Drawing Sheets

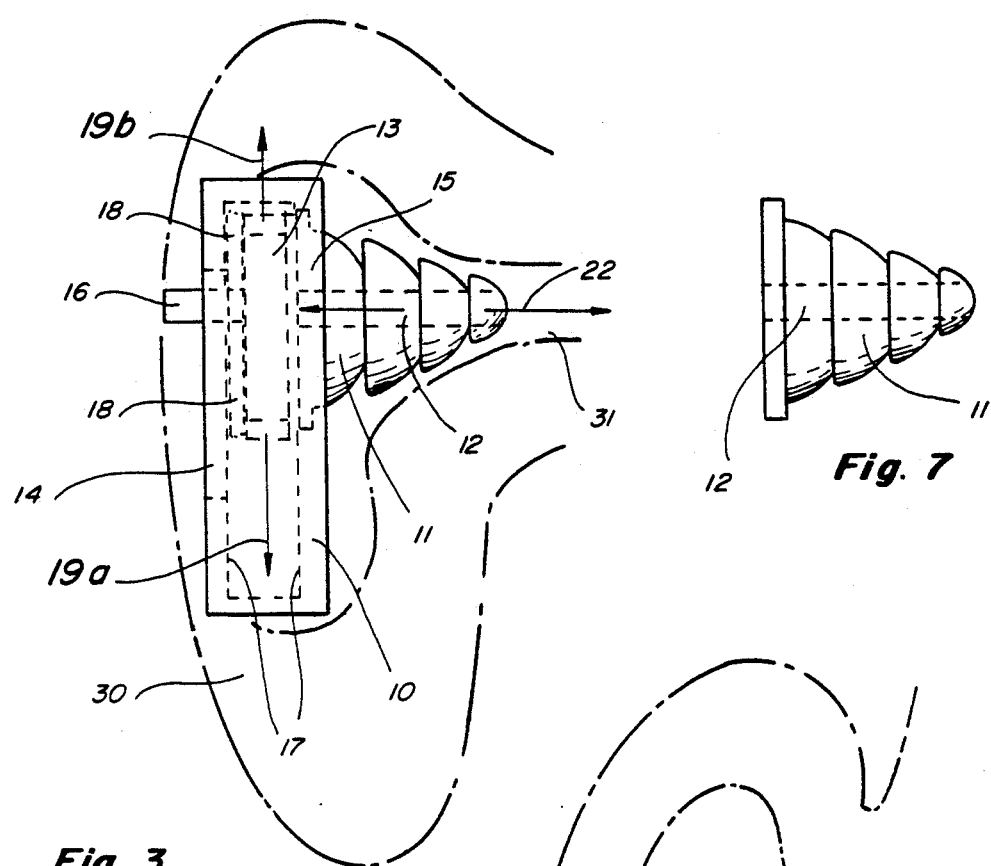
Fig. 3
Fig. 7
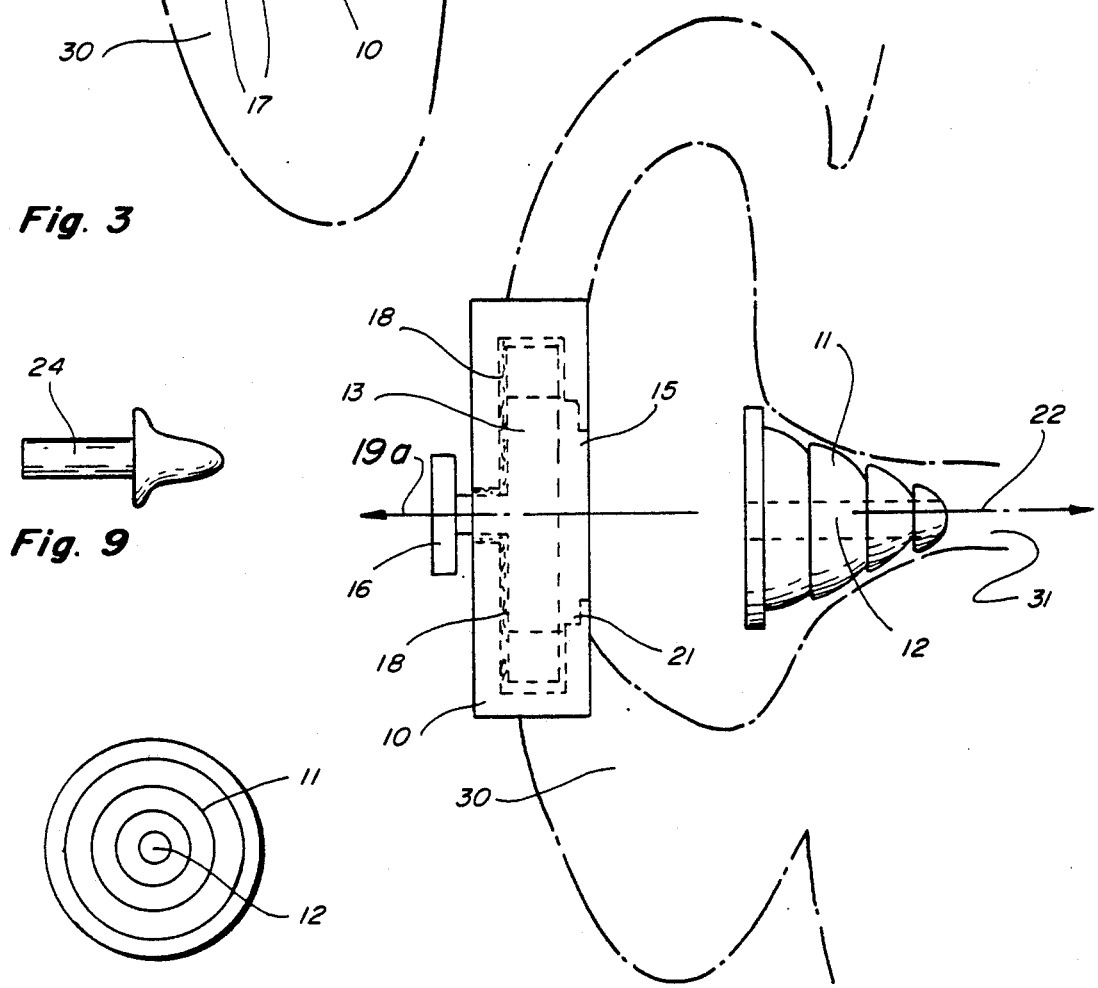
Fig. 9
Fig. 6
Fig. 4

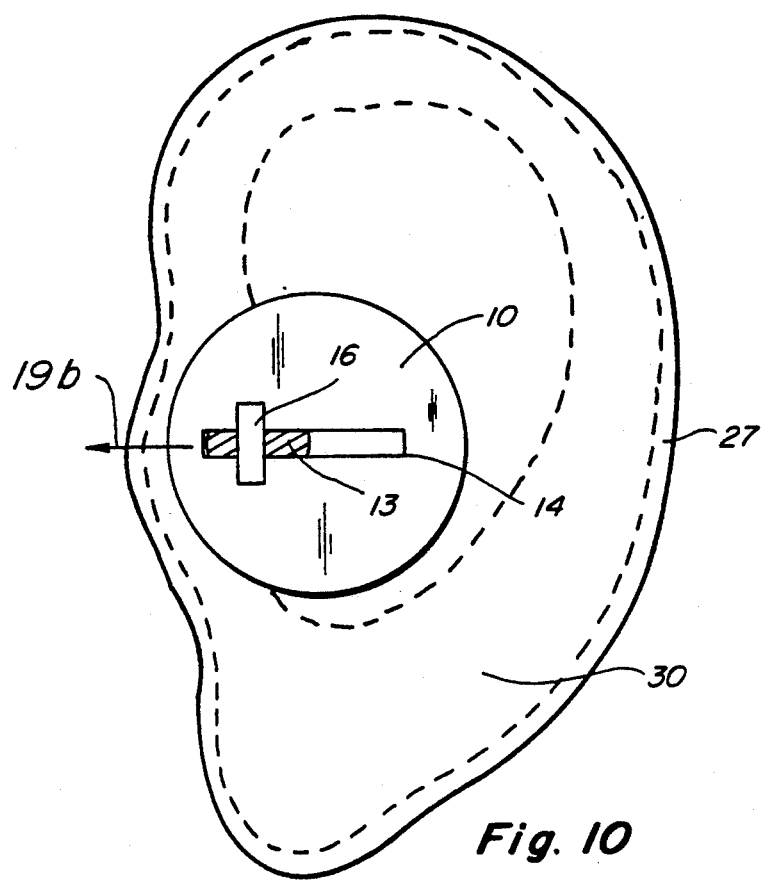
Fig. 10
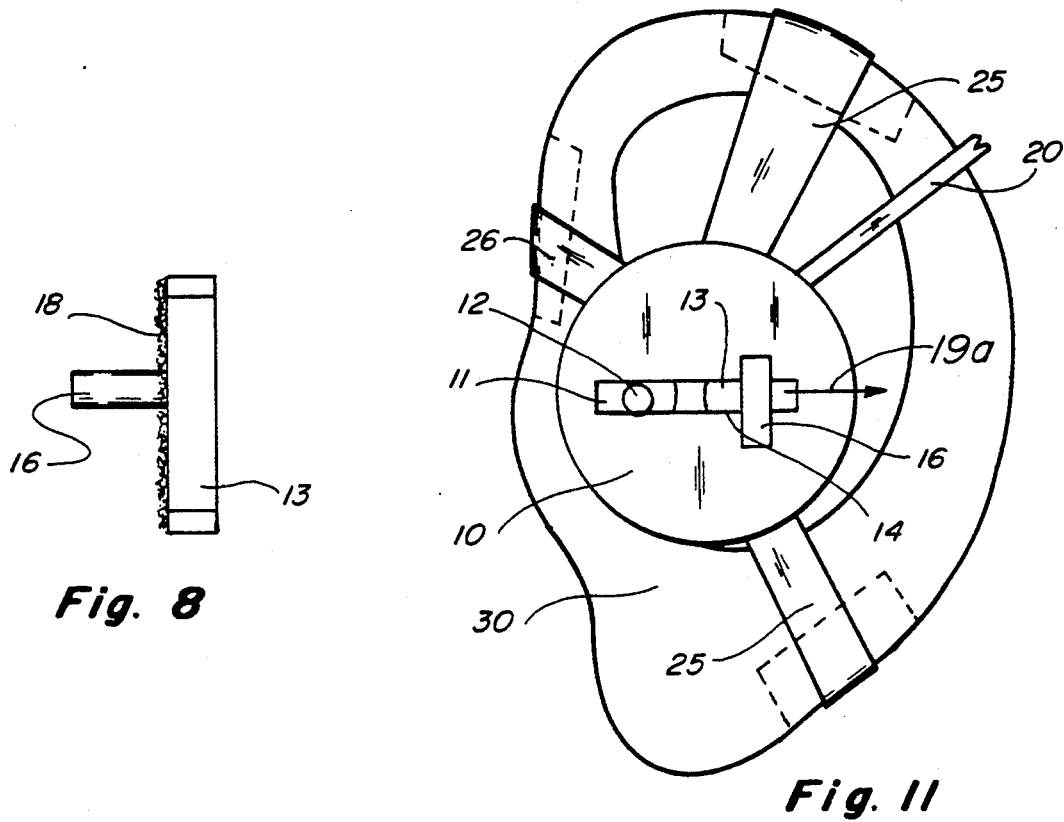
Fig. 8
Fig. 11

SLIDING VALVE EAR PLUG

BACKGROUND OF THE INVENTION

1. Field of the Invention

The subject invention wholly pertains to an area noise ear device used to facilitate hearing protection.

2. Description of Related Art

Many types of noise reducers are used in industry, recreation and business. The first ones were probable wads of cotton. One such earplug now reduces loud sounds 27 decibels (when used as directed). Besides being painful noise is dangerous. When you lose your hearing it will never come back. Loud sounds will hasten that loss. Hearing can be saved using the proper precautions and aids. Solid earplug aids have limitations this improved invention will overcome. Some earplugs are uncomfortable. Some are hard to put in and keep in. Once a wearer has them in, to hear something the person has to take them out. They get dirty quickly from use and as a result get pitched more than once when a person should have them in for ear protection. These and other objections I will elaborate on later on the state of the art of hearing protection today.

SUMMARY OF THE INVENTION

To avoid hearing and safety limitations one of the objectives of this improved invention is to give the wearer the option of hearing with an earplug still in the ear yet being able to keep out noise when or if the wearer desires with an ease not achieved with solid earplug protection.

An object is to help the wearer from taking the earplug out so much with the unsanitary collection of dirt and grease spoiling the earplug.

An object is for the person not to lose them, at other times quit wearing them entirely by taking them out so much.

An object would be wearability in that the invention wouldn't have to be taken in and out of their ears until an ear canal was rubbed sore trying to stop loud sporadic noises.

A supportive structure encompassing the ear attached to the invention made of wires, straps or other fixtures would be an object of the invention enhancing its use, comfort and stability.

In accordance these and other objects of the novel invention are provided by a improved method of shutting out noise and letting in sounds.

BRIEF DESCRIPTION OF THE DRAWINGS

FIG. 3 is a top view along the line 3—3 in FIG. 2.

FIG. 4 is a side view along the line 4—4 in FIG. 1.

FIG. 6 is a exploded side view of another part inside the device.

FIG. 7 is another top view of a part inside the device.

FIG. 8 is a exploded top view of a part inside the device.

FIG. 9 is an exploded side view of a part that could be substituted for another part.

FIG. 10 is a side view of parts made claim to in the application.

FIG. 11 is a side view of parts made claim to in the application.

DESCRIPTION OF THE PREFERRED EMBODIMENT

Figure 1:
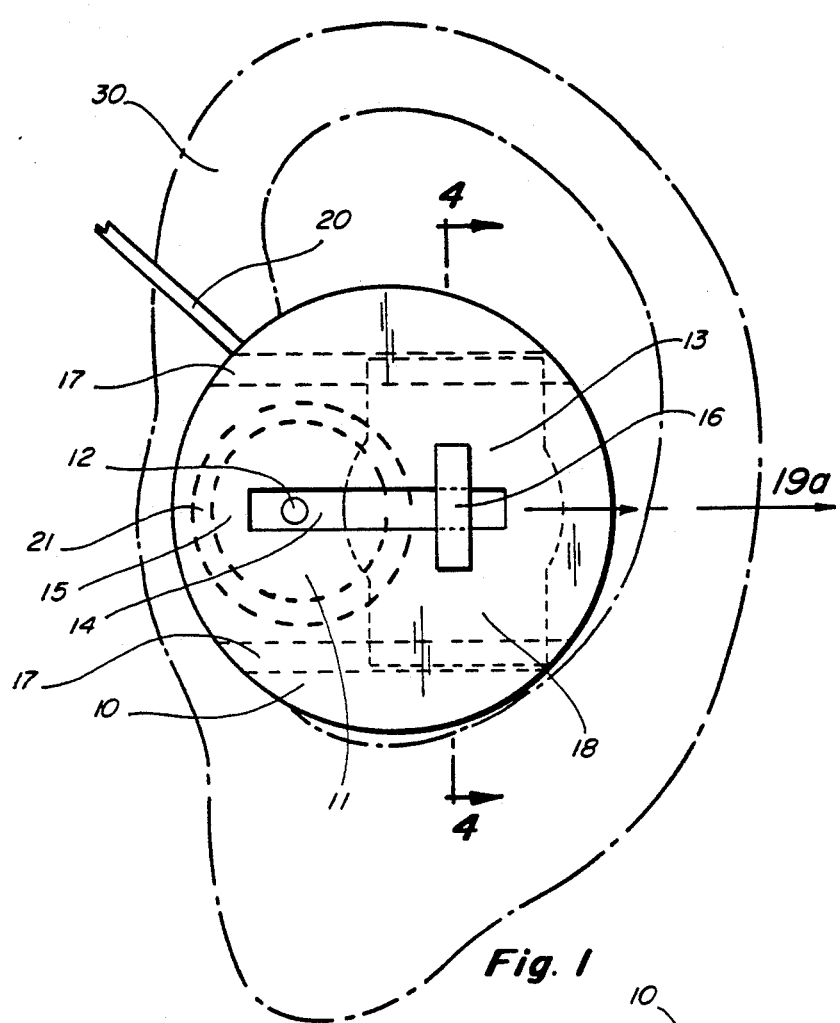
FIG. 1 is a side view of the invention with the valve in the open position.
Figure 5:
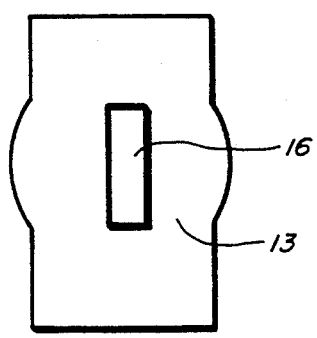
FIG. 5 is a exploded side view of a part inside the device.

Referring to FIGS. 1-11 the earplug embodying the invention comprising a sound path 22 for safety, health and personal use is a body 10, an ear plug 11 with a earplug hole 12 of suitable size. The earplug 11 is connected in hole 15 and counterbore 21 in body 10 next to the ear 30 in FIG. 3. Sliding valve 13 with fingerlatch 16 attached part exploded view shown in FIG. 5. Earplug 11 with earplug hole 12 in FIGS. 6,3 and 4. The fingerlatch 16 and sliding valve 13 move in tandem in the parallel valve guides 17 along the adjacent wall to ear 30 of body 10 and fingerlatch open slot 14 in arrow direction 19a, b; opening the invention in FIG. 1 and closing it in FIG. 2. A noise absorbing material 18 is connected permanently to the sliding valve 13. The connecting cord 20 is attached to each of two earplug inventions.

More specifically the invention of an earplug 11 with a suitable hole 12 is inserted into a person's ear canal 31 in FIGS. 3,4 with the body 10 fitting into the outer ear 30 FIG. 1,3,4. The earplug 11 is connected to the body 10 in the hole 15 and counterbore 21 in wall of body 10 next to the ear 30 which encases the earplug 11. The sliding valve 13 in the open position is connected to the fingerlatch 16 riding in the two valve guides 17 situated in the body wall next to the ear 30. The fingerlatch slotted hole 14 in body 10 with earplug hole 12 provides an opening for sound 22 through the invention to the wearer's eardrums in FIGS. 1 and 4.

Figure 2:
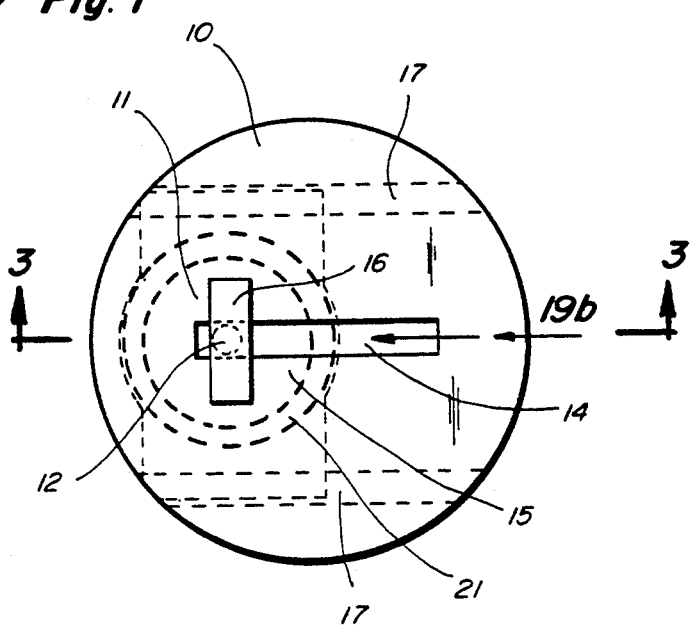
FIG. 2 is a side view with the valve in the body housing closed over the sound path.

Referring to FIG. 2 in another embodiment the earplug hole 12 is closed by the sliding valve 13 and moved by the fingerlatch 16 connected to the sliding valve 13 along parallel valve guides 17 in body 10 and fingerlatch slot opening 14 in body 10 in the direction of arrow 19b. The sliding valve 13 is in reverse of FIG. 1 in that position.

In reverse the body 10 with sliding valve 13 and fingerlatch 16 in sectional view 3—3 of FIG. 2 sound 22 is stopped by sliding valve 13 to the wearer of the invention. Sound deadening material 18 is shown on the sliding valve 13 to help stop sound 22 against the sliding valve 13. Sound 22 is stopped through the earplug hole 12 situated in hole 15 in body 10 with fingerlatch 16 in place in fingerlatch slotted hole 14.

The earplug 11 with a suitable earplug hole 12 would be connected to a body 10 in a body hole 15 and counterbore 21 in the body 10 and in conjunction with the fingerlatch slotted hole 14 in body 10 let sound 22 through the body 10 and earplug hole 12 to the wearer as in sectional view 4—4 of FIG. 1.

The sliding valve 13 is covered with a absorbing material 18 permanently to keep out noise and is rubbing against the opposite side of body 10 from the adjacent side of body 10 next to the ear 30 in FIGS. 3, 4. The sound deadening material 18 has a cushioning effect on the sliding valve 13 when moved, rubbing against the body 10 putting pressure on the earplug 11 and earplug hole 12 to keep out noise when in the closed position. A cord 20 of proper strength material would connect both earplugs to keep them together when the invention is not in use.

FIG. 1 shows the sliding valve 13 in body 10 positioned in valve guides 17 in an open position. The fingerlatch slotted hole 14 with earplug hole 12 in earplug 11 encased in hole 15 and counterbore 21 would let outside sound through to wearer of the invention without the wearer taking the earplug 11 out of his ear canal 31. This would help to keep the earplug 11 from getting dirty with a lot of handling. The invention would not get mislaid and lost so much. The wearer would more likely wear a clean earplug thus protecting his hearing better and for longer periods by keeping the invention in his ears longer and enjoying the objects it provides. Objects like being able to hear when the wearer wanted to without removing the invention. Being able to leave the invention in his ears and yet able to hear with the earplugs 11 still in.

Typically the earplug 11 with hole 12 would support its own weight of the earplug 11 in ear canal 31, body 10 fitted to the inner ear 30 that encloses sliding valve 13 with any other parts. In another embodiment parts of the ear canal 31 and outer ear 30 would help hold a suitable shaped body 10 with supplemental supports 25, 26 and 27 in FIGS. 10 and 11.

The ear plug shown in FIG. 1, FIGS. 6 and 7 is one type of solid earplug referred to and is made by the Cabot Safety Corporation of Indianapolis, Ind. (ULTRA FIT Model 4000C). It is an embodiment of one shape of earplug that could be attached to the body 10 of the invention in the hole opening 15 with a suitable size hole 12 in it to let sound 22 through to the wearer of the invention. It is made of rubber and would fit comfortably. Body 10, sliding valve 13 plus the earplug 11 with earplug hole 12 connected together with other parts would be one working piece fitted for ear canal 31 and outer ear 30 for size and comfort.

FIG. 8 shows sound deadening material 18 on sliding valve 13 to help deaden noise that might enter invention through fingerlatch slot opening 14, around the sliding valve 13 and earplug hole 12 to the wearer.

In another embodiment to stop the sound from going through the invention shown in FIG. 9 with the sliding valve 13 removed a solid plug 24 could be manually placed in the earplug hole 12. Removing the plug 24 in the earplug hole 12 of the invention would let sound 22 through to the wearer without the wearer taking the ear plug 11 with earplug hole 12 encased in body 10 out of his ear canal 31. This and other types of valves like the sliding valve 13, sliding or otherwise could be used to let sound 22 through the invention or stop sound 22 by closing the earplug hole 12.

A valve could rotate on a pivot point to an open and closed position over the earplug hole 12 in the body 10. A type of valve could open and close on hinges over the earplug hole 12 like a refrigerator door as an example, etc. Although the invention is described with respect to a preferred embodiment, modifications thereto will be apparent to those skilled in the art. Therefore, the scope of the invention is to be determined by reference to the claims which follow.

What is claimed is:

1. A hearing protection device comprising:
    a pair of earplugs each having a hole therethrough,
    a body defining an enclosure connected to each earplug,
    said body having a longitudinal slot and guide means, said slot and said hole together defining a sound passage,
    a movable valve disposed inside said enclosure,
    a fingerlatch supported in said slot and connected to said movable valve for sliding said valve along said guide means from one position to another to open and close said sound passage,
    a sound deadening material covering a portion of said movable valve for keeping out sound when said sound passage is closed, and a cord to attach said pair of earplugs together.

2. The device of claim 1 further including a supporting means for comfortably holding said hearing protection device in the ear canal.

* * * * *